US009345671B2

(12) United States Patent
Takagi et al.

(10) Patent No.: US 9,345,671 B2
(45) Date of Patent: *May 24, 2016

(54) ADIPONECTIN PRODUCTION ENHANCER

(75) Inventors: Toshiyuki Takagi, Shinagawa-ku (JP);
Iichiro Shimomura, Toyonaka (JP);
Yuji Matsuzawa, Takarazuka (JP);
Tohru Funahashi, Suita (JP)

(73) Assignee: Daiichi Sankyo Company, Limited, Chuo-ku (JP)

( * ) Notice: Subject to any disclaimer, the term of this patent is extended or adjusted under 35 U.S.C. 154(b) by 350 days.

This patent is subject to a terminal disclaimer.

(21) Appl. No.: 10/555,076

(22) PCT Filed: Apr. 27, 2004

(86) PCT No.: PCT/JP2004/006100
§ 371 (c)(1),
(2), (4) Date: Mar. 2, 2006

(87) PCT Pub. No.: WO2004/096278
PCT Pub. Date: Nov. 11, 2004

(65) Prior Publication Data
US 2007/0059357 A1 Mar. 15, 2007

(30) Foreign Application Priority Data

Apr. 28, 2003 (JP) ................................. 2003-123768
Jan. 20, 2004 (JP) ................................. 2004-012265

(51) Int. Cl.
| A61K 31/047 | (2006.01) |
| A61K 31/10 | (2006.01) |
| A61K 31/191 | (2006.01) |
| A61K 31/21 | (2006.01) |
| A61K 31/22 | (2006.01) |
| A61K 31/495 | (2006.01) |
| A61K 31/505 | (2006.01) |
| A61K 31/00 | (2006.01) |
| A61K 31/366 | (2006.01) |
| A61K 31/40 | (2006.01) |
| A61K 31/404 | (2006.01) |
| A61K 31/4418 | (2006.01) |
| A61K 31/47 | (2006.01) |

(52) U.S. Cl.
CPC ............... *A61K 31/00* (2013.01); *A61K 31/047* (2013.01); *A61K 31/10* (2013.01); *A61K 31/191* (2013.01); *A61K 31/21* (2013.01); *A61K 31/22* (2013.01); *A61K 31/366* (2013.01); *A61K 31/40* (2013.01); *A61K 31/404* (2013.01); *A61K 31/4418* (2013.01); *A61K 31/47* (2013.01); *A61K 31/495* (2013.01); *A61K 31/505* (2013.01)

(58) Field of Classification Search
CPC ... A61K 31/047; A61K 31/10; A61K 31/191; A61K 31/21; A61K 31/22; A61K 31/495; A61K 31/505

USPC .......................................................... 514/460
See application file for complete search history.

(56) References Cited

U.S. PATENT DOCUMENTS

| 4,231,938 | A | | 11/1980 | Monaghan et al. | |
| 4,346,227 | A | | 8/1982 | Terahara et al. | |
| 4,444,784 | A | | 4/1984 | Hoffman et al. | |
| 4,739,073 | A | | 4/1988 | Kathawala | |
| 5,006,530 | A | | 4/1991 | Angerbauer et al. | |
| 5,130,333 | A | * | 7/1992 | Pan et al. ...................... | 514/460 |
| 5,260,440 | A | | 11/1993 | Hirai et al. | |
| 5,273,995 | A | | 12/1993 | Roth | |
| 5,298,497 | A | | 3/1994 | Tschollar | |
| 5,643,868 | A | | 7/1997 | Weiner | |
| 5,798,375 | A | | 8/1998 | Tsujita | |
| 5,854,259 | A | | 12/1998 | Fujikawa et al. | |
| 5,856,336 | A | | 1/1999 | Fujikawa et al. | |
| 6,020,382 | A | * | 2/2000 | Doebber et al. ............... | 514/708 |
| 6,130,214 | A | * | 10/2000 | Lohray et al. ............... | 514/224.2 |
| 6,159,997 | A | | 12/2000 | Tsujita | |
| 6,384,062 | B1 | * | 5/2002 | Ikeda et al. .................... | 514/342 |
| 6,414,126 | B1 | * | 7/2002 | Ellsworth et al. ............ | 536/17.2 |

FOREIGN PATENT DOCUMENTS

| EP | 0 671 170 A1 | 9/1995 |
| EP | 1275388 A1 | 8/1998 |
| EP | 0956897 A1 | 11/1999 |
| EP | 1 325 745 A1 | 4/2002 |
| EP | 1325745 A1 | 7/2003 |
| JP | 04-282324 A | 10/1992 |
| JP | 9-71540 A | 3/1997 |
| JP | 20011294526 A | 10/2001 |
| WO | 95/13063 A1 | 5/1995 |
| WO | 00/45818 A1 | 8/2000 |
| WO | WO 00/56403 A1 | 9/2000 |
| WO | WO 01/76573 A2 | 10/2001 |
| WO | 02/30425 A1 | 4/2002 |
| WO | 2004/052368 A1 | 6/2004 |

OTHER PUBLICATIONS

Schulze et al., Adiponectin and Future Coronary Heart Disease Events Among Men With Type 2 Diabetes, Diabetes (2005), 54:534-539, printed pp. 1-6.*

(Continued)

*Primary Examiner* — Yong Chong
(74) *Attorney, Agent, or Firm* — Christensen O'Connor Johnson Kindness PLLC; Juan Zheng; George Renzoni

(57) ABSTRACT

The present invention provides a pharmaceutical composition for enhancement of adiponectin production, treatment or prevention of hypoadiponectinemia, and the like, comprising as an active ingredient an HMG-CoA reductase inhibitor.

12 Claims, No Drawings

(56) References Cited

OTHER PUBLICATIONS

Orsi et al. (Simvastatin-Associated Memory Loss) Pharmacotherapy 21(6): 767-769, 2001, printed pp. 1-3, especially p. 2, paragraphs 1-3).*

Kadowaki et al., Adiponectin and Adiponectin Receptors, Endocrine Reviews 26 (3): 439-451, especially, printed pp. 1-41, especially p. 1, see abstract, 2005.*

Saito et al., Statin reverses reduction of adiponectin receptor expression in infracted heart and in TNF-α-treated cardiomyocytes in association with improved glucose uptake, Am J Physiol Heart Circ physiol 293: H3490-H3497, 2007, printed pp. 1-13, see abstract.*

Dumont, A.S., et al., "Improvement of Endothelial Function in Insulin-Resistant Carotid Arteries Treated With Pravastatin," Journal of Neurosurgery 95:466-471, Sep. 2001.

"HMG-CoA Reductase Inhibitors," Express Scripts ©, DrugDigest © 2007, <http://www.drugdigest.org/DD/Comparison/NewComparison/0,10621,37-15,00.html> [retrieved Aug. 2, 2007].

Sowers, J.R., "Effects of Statins on the Vasculature: Implications for Aggressive Lipid Management in the Cardiovascular Metabolic Syndrome," The American Journal of Cardiology 91(4A):14B-22B, Feb. 20, 2003.

Usui, H., et al., "HMB-CoA Reductase Inhibitor Ameliorates Diabetic Nephropathy by its Pleiotropic Effects in Rats," Nephrology Dialysis Transplantation 18:265-272, 2003.

Chapman, M.J., and F. McTaggart, "Optimizing the Pharmacology of Statins: Characteristics of Rosuvastatin," Atherosclerosis Supplements 2:33-37, 2002.

F. McTaggart, et al., "Preclinical and Clinical Pharmacology of Rosuvastatin, a New 3-Hydroxy-3-Methylglutaryl Coenzyme a Reductase Inhibitor," The American Journal of Cardiology 87(5A): 28B-32B, Mar. 2001.

Arita, Y., et al., "Adipocyte-Derived Plasma Protein Adiponectin Acts as a Platelet-Derived Growth Factor-BB-Binding Protein and Regulates Growth Factor-Induced Common Postreceptor Signal in Vascular Smooth Muscle Cell," Circulation 105:28933-2898, Jun. 18, 2002.

Arita, Y., et al., "Paradoxical Decrease of an Adipose-Specific Protein, Adiponectin, in Obesity,"Biochemical and Biophysical Research Communications 257(1):79-83, 1999.

Bellosta, S., et al., "Pleiotropic Effects of Statins in Atherosclerosis and Diabetes," Diabetes Care 23(Suppl. 2) Apr. 2000, 1 p. (abstract), retrieved from <http://www.ncbi.nlm.nih.gov/entrez/query.fcgi?cmd=Retrieve&db=pubmed&dopt=Abstract&list_uids=10860194&query_hl=2&itool=pubmed_DocSum> [retrieved Oct. 5, 2005].

Berg, A.H., et al., "The Adipocyte-Secreted Protein Acrp30 Enhances Hepatic Insulin Action," Nature Medicine 7(8):947-953, Aug. 2001.

Chaudhuri, A., "Vascular Reactivity in Diabetes Mellitus," Current Diabetes Reports 2:305-310, 2002.

Cingözbay, B.Y., et al., "Effects of Fluvastatin Treatment on Insulin Sensitivity in Patients With Hyperlipidaemia," Journal of International Medical Research 30:21-25, 2002.

Combs, T.P., et al., "Endogenous Glucose Production Is Inhibited by the Adipose-Derived Protein Acrp30," Journal of Clinical Investigation 108(12):1875-1881, Dec. 2001.

Freeman, D.J., et al., "Pravastatin and the Development of Diabetes Mellitus: Evidence for a Protective Treatment Effect in the West of Scotland Coronary Prevention Study," Circulation 103:357-362, Jan. 23, 2001.

Hotta, K., et al., "Circulating Concentrations of the Adipocyte Protein Adiponectic Are Decreased in Parallel With Reduced Insulin Sensitivity During The Progression to Type 2 Diabetes in Rhesus Monkeys," Diabetes 50:1126-1133, May 2001.

Komai, T., "Effect of Statins on Glucose Metabolism," Bio Clinica 17(10):68-73, 2002.

Kondo, H., et al., "Association of Adiponectin Mutation With Type 2 Diabetes: A Candidate Gene for the Insulin Resistance Syndrome," Diabetes 51:2325-2328, Jul. 2002.

Linday, R.S., et al., "Adiponectin and Development of Type 2 Diabetes in the Pima Indian Population," Lancet 360:57-58, Jul. 6, 2002.

MacMahon, S., et al., "Effects of Lowering Average or Below-Average Cholesterol Levels on the Progression of Carotid Atherosclerosis, Levels on the Progression of Carotid Atherosclerosis: Results of the LIPID Atherosclerosis Substudy," Circulation 97:1784-1790, May 12, 1998.

Maeda, K., et al., "cDNA Cloning and Expression of Novel Adipose Specific Collagen-Like Factor, apM1 (Adipose Most Abundant Gene Transcript 1)," Biochemical and Biophysical Research Communications 221(2):286-289, 1996.

Maeda, N., et al., "PPARγ0 Ligands Increase Expression and Plasma Concentrations of Adiponectin, an Adipose-Derived Protein," Diabetes 50:2094-2099, Sep. 2001.

Mangaloglu, L., et al., "Treatment With Atorvastatin Ameliorates Hepatic Very-Low-Density Lipoprotein Overproduction in an Animal Model of Insulin Resistance, the Fructose-Fed Syrian Golden Hamster: Evidence That Reduced Hypertriglyceridemia Is Accompanied by Improved Hepatic Insulin Sensitivity," Metabolism 51(4):409-418, Apr. 2002.

McFarlane, S.I., et al., "Clinical Review 145: Pleiotropic Effects of Statins: Lipid Reduction and Beyond," Journal of Clinical Endocrinology & Metabolism 87(4):1451-1458, Apr. 2002.

McVeigh, G.E., and J.N. Cohn, "Endothelial Dysfunction and the Metabolic Syndrome," Current Diabetes Reports 3:87-92, 2003.

Okamoto, Y., et al., "Adiponectin Reduces Atherosclerosis in Apolipoprotein E-Deficient Mice," Circulation 106:2767-2770, Nov. 26, 2002.

Ouchi, N., et al., "Adipocyte-Derived Plasma Protein, Adiponectin, Suppresses Lipid Accumulation and Class A Scavenger Receptor Expression in Human Monocyte-Derived Macrophages,"Circulation 103:1057-1063, Feb. 27, 2001.

Ouchi, N., et al., "Adiponectin, an Adipocyte-Derived Plasma Protein, Inhibits Endothelial NF-κB Signaling Through a cAMP-Dependent Pathway," Circulation 102:1296-1301, Sep. 12, 2000.

Ouchi, N., et al., "Novel Modulator for Endothelial Adhesion Molecules: Adipocyte-Derived Plasma Protein Adiponectin," Circulation 100:2473-2476, Dec. 21/28, 1999.

Paolisso, G., et al., "Effects of Simvastatin and Atorvastatin Administration on Insulin Resistance and Respiratory Quotient in Aged Dyslipidemic Non-Insulin Dependent Diabetic Patients," Atherosclerosis 150:121-127, 2000.

Reaven, G.M., "Role of Insulin Resistance in Human Disease," Diabetes 37:1595-1607, Dec. 1988.

Ross, R., "The Pathogenesis of Atherosclerosis: A Perspective for the 1990s," Nature 362:801-809, Apr. 29, 1993.

Shepherd, J., et al., "Pravastatin in Elderly Individuals at Risk of Vascular Disease (Prosper): a Randomised Controlled Trial," Lancet 360:1623-1630, Nov. 23, 2003.

Sorisky, A., "Molecular Links Between Obesity and Cardiovascular Disease," American Journal of Therapeutics 9:516-521, 2002.

Weyer, C., et al., "Hypoadiponectinemia in Obesity and Type 2 Diabetes: Close Association With Insulin Resistance and Hyperinsulinemia," Journal of Clinical Endocrinology & Metabolism 86(5):1930-1935, 2001.

Yamauchi, T., et al., "The Fat-Derived Hormone Adiponectin Reverses Insulin Resistance Associated With Both Lipoatrophy and Obesity," Nature Medicine 7(8):941-946, Aug. 2001.

Yokota, T., et al., "Adiponectin, a New Member of the Family of Soluble Defense Collagens, Negatively Regulates the Growth of Myelomonocytic Progenitors and the Functions of Macrophages," Blood 96(5):1723-1732, Sep. 1, 2000.

Zoccali, C., et al., "Adiponectin, Metabolic Risk Factors, and Cardiovascular Events Among Patients With End-Stage Renal Disease," Journal of the American Society of Nephrology 13:134-141, 2002.

Office Action mailed Jul. 29, 2015, in corresponding Canadian Patent Application No. 2,524,134, filed Apr. 27, 2004, 5 pages.

Ballantyne, C.M., et al., "Efficacy of Rosuvastatin 10 mg in Patients With the Metabolic Syndrome," American Journal of Cardiology 91(5A):25C-27C, Mar. 2003.

Deedwania, P., and D. Hunninghake, "Comparative Effects of Statins on Atherogenic Dyslipidemia in Patients With the Metabolic Syndrome," Journal of the American College of Cardiology 43(5, Suppl

(56) References Cited

OTHER PUBLICATIONS

A):485A, Mar. 2004 (presented at the 53rd Annual Scientific Session of the American College of Cardiology, New Orleans, Mar. 7-10, 2004) (Abstract 820-1).
Drossos, T., et al., "Results of Pravastatin on Metabolic Parameters of Patients With Diabetes Mellitus Type II Under Simultaneous Treatment With Glybenclamide," Atherosclerosis 144:205, May 1999 (Abstract).
Giannoukakis, N., and P.D. Robbins, "Gene and Cell Therapies for Diabetes Mellitus," Biodrugs 16(3):149-173, 2002.
Homko, C.J., et al., "Effects of Free Fatty Acids on Glucose Uptake and Utilization in Healthy Women," Diabetes 52(2):487-491, Feb. 2003.
Hunninghake, D.B., et al., "Comparative Effects of Simvastatin and Atorvastatin in Hypercholesterolemic Patients With Characteristics of Metabolic Syndrome," Clinical Therapeutics 25(6):1670-1686, Jun. 2003.
Inoue, Y., et al., "A Multi-Centre Study of the Efficacy and Safety of Pravastatin in Hypercholesterolaemic Patients With Non-Insulin-Dependent Diabetes Mellitus," Current Medical Research and Opinion 13(4):187-194, 1994.
Merrill, G.F., et al., "AICA Riboside Increases AMP-Activated Protein Kinase, Fatty Acid Oxidation, and Glucose Uptake in Rat Muscle," American Physiological Society 273(6 Pt 1):E1107-E1112, Dec. 1997.
Newman, C., et al., "Efficacy of Atorvastatin in Dyslipidemic Patients With Metabolic Syndrome in the ACCESS Study," Diabetes 52(Suppl 1):A494, 2003 (presented at the 63rd Scientific Sessions of the American Diabetes Association, New Orleans, Jun. 13-17, 2003) (Abstract 2141-PO).
Olsson, A.G., et al., "Rosuvastatin: A Highly Effective New HMG-CoA Reductase Inhibitor," Cardiovascular Drug Reviews 20(4):303-328, Jan. 2002.
Paniagua, J.A., et al., "Cerivastatin Improves Insulin Sensitivity and Insulin Secretion in Early-State Obese Type 2 Diabetes," Diabetes 51(8):2596-2603, Aug. 2002.
Sugimoto, T., "Pravastatin Versus Simvastatin in Hyperlipidemic Patients With Type 2 Diabetes Mellitus," Current Therapeutic Research 60(7):404-413, Jul. 1999.
Vázquez, M., et al., "Experimental Approaches to Study PPARγ Agonists as Antidiabetic Drugs," Methods and Findings in Experimental and Clinical Pharmacology 24(8):515-523, Oct. 2002.
Zhang, B., et al., "Discovery of a Small Molecule Insulin Mimetic With Antidiabetic Activity in Mice," Science 824(5416):974-977, May 1999.
Supplementary European Search Report dated Jul. 8, 2009, in corresponding European Application No. EP 04 72 9769, filed Apr. 27, 2004.
Glorioso, N., et al., "Effect of the HMG-CoA Reductase Inhibitors on Blood Pressure in Patients With Essential Hypertension and Primary Hypercholesterolemia," Hypertension 34(6):1281-1286, Dec. 1999.
Komai, T., "Effect of Statins on Glucose Metabolism," Bio Clinica 17(10):918-923, 2002, [English translation of pertinent paragraphs].
Shiomi, M., et al., "Combination Treatment With Troglitazone, an Insulin Action Enhancer, and Pravastatin, an Inhibitor of HMG-CoA Reductase, Shows a Synergistic Effect on Atherosclerosis of WHHL Rabbits," Atherosclerosis 142(2):345-353, Feb. 1999.

* cited by examiner

ADIPONECTIN PRODUCTION ENHANCER

TECHNICAL FIELD

The present invention relates to a pharmaceutical composition containing as an active ingredient one or more HMG-CoA reductase inhibitor(s) for enhancement of adiponectin production; treatment or prevention of hypoadiponectinemia; improvement of insulin resistance; treatment or prevention of Syndrome X or metabolic syndrome; treatment or prevention of diabetes, diabetes complications (including retinopathy, nephropathy, neuropathy, cataract, and coronary artery disease), hypertension, obesity or arteriosclerosis; or treatment or prevention of diabetes, diabetes complications (including retinopathy, nephropathy, neuropathy, cataract and coronary artery disease), hypertension, obesity or arteriosclerosis caused by hypoadiponectinemia or insulin resistance syndrome, and a method comprising administration of an effective amount of one or more HMG-CoA reductase inhibitor(s) to a warm-blooded animal for enhancement of adiponectin production; treatment or prevention of hypoadiponectinemia; improvement of insulin resistance; treatment or prevention of Syndrome X or metabolic syndrome; treatment or prevention of diabetes, diabetes complications (including retinopathy, nephropathy, neuropathy, cataract, and coronary artery disease), hypertension, obesity or arteriosclerosis; or treatment or prevention of diabetes, diabetes complications (including retinopathy, nephropathy, neuropathy, cataract and coronary artery disease), hypertension, obesity or arteriosclerosis caused by hypoadiponectinemia or insulin resistance syndrome.

BACKGROUND ART

Adiponectin is a protein that is specifically produced and secreted from adipocytes, and is intimately involved in energy balance and glucose or lipid metabolism (Maeda, K. et al., Biochemical and Biophysical Research Communications, 1996, 221, 286-289). In actuality, in patients with circulatory diseases, diabetes, obesity, etc., blood adiponectin concentration decreases (Ouchi, N. et al., Circulation, 1999, 100, 2473-2476; Lindsay, R. S. et al., Lancet, 2002, 360, 57-58; Arita, Y. et al., Biochemical and Biophysical Research Communications, 1999, 257, 79-83). In addition, kidney disease patients exhibiting low blood adiponectin concentrations are known to have a higher mortality rate due to circulatory diseases than patients with high blood adiponectin concentrations (Zoccali, C. et al., Journal of American Society of Nephrology, 2002, 13, 134-141). Thus, disease states having decreased blood adiponectin concentrations, namely hypoadiponectinemia, are thought to be intimately related to lifestyle diseases such as circulatory diseases (arteriosclerosis, hypertension, etc.), diabetes or obesity, and are believed to be one of their basic causes (Weyer, C. et al., The Journal of Clinical Endocrinology & Metabolism, 2001, 86, 1930-1935; Hotta, K. et al., Diabetes, 2001, 50, 1126-1133). Thus, the treatment or prevention of hypoadiponectinemia is also useful in the treatment or prevention of the aforementioned lifestyle diseases caused by hypoadiponectinemia.

Adiponectin is known to have actions of suppressing adhesion of THP-1 cells to vascular endothelial cells, expression of adhesion molecules, differentiation of vascular smooth muscle cells, macrophage foam cell formation, and the like (Ouchi, N. et al., Circulation, 1999, 100, 2473-2476; Ouchi, N. et al., Circulation 2001, 103, 1057-1063; Arita, Y. et al., Circulation 2002, 105, 2893-2898; Ouchi, N. et al., Circulation, 2000, 102, 1296-1301; Yokota, T. et al., Blood, 2000, 96, 1723-1732). These biological phenomena are intrinsic phenomena that occur during the initial stage of the onset of arteriosclerosis (Ross, R. et al., Nature, 1993, 362, 801-809), and the inhibitory effects demonstrated by adiponectin on these phenomena are extremely useful for the treatment or prevention of arteriosclerosis. In addition, increasing adiponectin concentration has been shown to have therapeutic effects on arteriosclerosis in an actual animal model (Okamoto, Y. et al., Circulation, 2002, 106, 2767-2770).

In addition, adiponectin is also intimately related to insulin resistance and diabetes (Kondo, H. et al., Diabetes, 2002, 51, 2325-2328). Insulin resistance is known to increase in the presence of hypoadiponectinemia (Weyer, C. et al., The Journal of Clinical Endocrinology & Metabolism, 2001, 86, 1930-1935; Hotta, K. et al., Diabetes, 2001, 50, 1126-1133), and in an animal model, administration of adiponectin is known to demonstrate glucose metabolism ameliorative action by having effects of improving insulin resistance, suppressing glucose production in the liver, and the like (Yamauchi, T., et al., Nature Medicine, 2001, 7, 941-946; Berg, A. H. et al., Nature Medicine, 2001, 7, 947-953; Combs, T. P. et al., Clinical Investigation, 2001, 108, 1875-1881). Thus, increasing blood adiponectin concentration is useful for the treatment or prevention of diabetes and diabetes complications caused thereby.

Diseases states that exhibit increased insulin resistance, namely insulin resistance syndrome, are considered to be a principal cause of diabetes as well as the fundamental cause of lifestyle diseases such as circulatory diseases (arteriosclerosis, hypertension, etc.) or obesity (McVeigh, G. E. et al., Current Diabetes Reports, 2003, 3, 87-92; Chaudhuri, A. et al., Current Diabetes Reports, 2002, 2, 305-310; Sorisky, A. et al., American Journal of Therapeutics, 2002, 9, 516-521), and improvement of insulin resistance plays an important role in the treatment or prevention of the aforementioned lifestyle diseases. In other words, improvement of insulin resistance is also useful for the treatment or prevention of the aforementioned lifestyle diseases caused by insulin resistance syndrome. As previously mentioned, since adiponectin has an action of improving insulin resistance (Yamauchi, T. et al., Nature Medicine, 2001, 7, 941-946), a medicament that enhances adiponectin production is useful for the treatment or prevention of insulin resistance syndrome, as well as the treatment or prevention of diabetes, diabetes complications, circulatory diseases (arteriosclerosis, hypertension, etc.) or obesity caused by insulin resistance syndrome.

In addition, the concepts of Syndrome X, metabolic syndrome, and the like have recently been advocated as disease states that increase the risk of coronary artery disease through a complex relationship with abnormal lipid metabolism diseases, diabetes, insulin resistance syndrome, and so forth (Reave, G. M., Diabetes, 1988, 37, 1595-1607; DeFronzo, R. A. et al., Diabetes Cara, 1991, 14, 173-194; Matsuzawa, Y., Nihon-Naikagaku-Zasshi (J. Jap. Soc. Internal Medicine), 1995, 84, 209-212). As previously described, since adiponectin is able to contribute to the treatment or prevention of the respective causes of Syndrome X, metabolic syndrome, and the like a medicament that enhances the production of adiponectin is also useful for the treatment or prevention of Syndrome X, metabolic syndrome, and the like.

On the basis of the above, a medicament that enhances adiponectin production has an action of improving insulin resistance and is useful as a pharmaceutical composition for enhancement of adiponectin production; treatment or prevention of hypoadiponectinemia; improvement of insulin resistance; treatment or prevention of Syndrome X or metabolic syndrome; treatment or prevention of diabetes, diabetes complications (including retinopathy, nephropathy, neuropathy, cataract, and coronary artery disease), hypertension, obesity or arteriosclerosis; or treatment or prevention of diabetes, diabetes complications (including retinopathy, nephropathy, neuropathy, cataract and coronary artery disease), hypertension, obesity or arteriosclerosis caused by hypoadiponectinemia or insulin resistance syndrome.

Although certain types of thiazolidine dione compounds or cannabinoid $CB_1$ receptor antagonists are known to demonstrate action of enhancing adiponectin production (for example, Maeda, N. et al., Diabetes, 2001, 50, 2094-2099; Bensaid, M. et al., Molecular Pharmacology, 2002, 360, 1623-1630; etc.), HMG-CoA reductase inhibitors have not been known to demonstrate adiponectin production enhancing action or therapeutic or preventive effects for hypoadiponectinemia.

HMG-CoA (3-hydroxy-3-methylglutaryl-CoA) reductase inhibitors are well-known hyperlipemia therapeutic medicaments (for example, U.S. Pat. No. 4,346,227, etc.). Statins are typical HMG-CoA reductase inhibitors, and disease preventive effects in humans have been confirmed in various clinical studies. For example, pravastatin has been reported to demonstrate effects (preventive effects) of suppressing the onset of arteriosclerosis, coronary artery disease and diabetes in a clinical study targeted at hyperlipemia patients (for example, MacMahon, S. et al., Circulation, 1998, 97, 1784-1790; Shepherd, J. et al., Lancet, 2002, 360, 1623-1630; Freeman, D. J. et al., Circulation, 2001, 103, 357-362; etc.).

However, HMG-CoA reductase inhibitors are not known to demonstrate therapeutic effects for arteriosclerosis or diabetes, or therapeutic or preventive effects for diabetes complications, hypertension or obesity.

In addition, although certain types of HMG-CoA reductase inhibitors have been reported to have an action of improving insulin resistance (for example, Mangaloglu, L. et al., Metabolism, Clinical and Experimental, 2002, 51, 409-418; Cingozbay, B. Y. et al., Journal of International Medical Research, 2002, 30, 21-25; Paolisso, G. et al., Atherosclerosis, 2000, 150, 121-127; etc.), pravastatin and rosuvastatin have heretofore not been known to have an action of improving insulin resistance.

DISCLOSURE OF THE INVENTION

The inventors of the present invention found that an HMG-CoA reductase inhibitor has superior adiponectin production enhancing action, and is useful as a pharmaceutical composition for enhancement of adiponectin production; treatment or prevention of hypoadiponectinemia; improvement of insulin resistance; treatment or prevention of Syndrome X or metabolic syndrome; treatment or prevention of diabetes, diabetes complications (including retinopathy, nephropathy, neuropathy, cataract, and coronary artery disease), hypertension, obesity or arteriosclerosis; or treatment or prevention of diabetes, diabetes complications (including retinopathy, nephropathy, neuropathy, cataract and coronary artery disease), hypertension, obesity or arteriosclerosis caused by hypoadiponectinemia or insulin resistance syndrome, thereby leading to completion of the present invention.

The present invention provides a pharmaceutical composition containing as an active ingredient one or more HMG-CoA reductase inhibitor(s), for enhancement of adiponectin production; treatment or prevention of hypoadiponectinemia; improvement of insulin resistance; treatment or prevention of Syndrome X or metabolic syndrome; treatment or prevention of diabetes, diabetes complications (including retinopathy, nephropathy, neuropathy, cataract, and coronary artery disease), hypertension, obesity or arteriosclerosis; or treatment or prevention of diabetes, diabetes complications (including retinopathy, nephropathy, neuropathy, cataract and coronary artery disease), hypertension, obesity or arteriosclerosis caused by hypoadiponectinemia or insulin resistance syndrome, and a method comprising administration of an effective amount of one or more HMG-CoA reductase inhibitor(s) to a warm-blooded animal for enhancement of adiponectin production; treatment or prevention of hypoadiponectinemia; improvement of insulin resistance; treatment or prevention of Syndrome X or metabolic syndrome; treatment or prevention of diabetes, diabetes complications (including retinopathy, nephropathy, neuropathy, cataract, and coronary artery disease), hypertension, obesity or arteriosclerosis; or treatment or prevention of diabetes, diabetes complications (including retinopathy, nephropathy, neuropathy, cataract and coronary artery disease), hypertension, obesity or arteriosclerosis caused by hypoadiponectinemia or insulin resistance syndrome.

The present invention is:

(1) a pharmaceutical composition for enhancement of adiponectin production comprising as an active ingredient one or more HMG-CoA reductase inhibitor(s);

(2) a pharmaceutical composition as (1), wherein the HMG-CoA reductase inhibitor is selected from the group consisting of pravastatin, lovastatin, simvastatin, fluvastatin, cerivastatin, atorvastatin, pitavastatin and rosuvastatin;

(3) a pharmaceutical composition as (1), wherein the HMG-CoA reductase inhibitor is a water-soluble HMG-CoA reductase inhibitor;

(4) a pharmaceutical composition as (1), wherein the HMG-CoA reductase inhibitor is selected from the group consisting of pravastatin or a derivative thereof and rosuvastatin or a derivative thereof;

(5) a pharmaceutical composition as (1), wherein the HMG-CoA reductase inhibitor is selected from the group consisting of pravastatin and rosuvastatin;

(6) a pharmaceutical composition as (1), wherein the HMG-CoA reductase inhibitor is pravastatin;

(7) a pharmaceutical composition for the treatment or prevention of hypoadiponectinemia comprising as an active ingredient one or more water-soluble HMG-CoA reductase inhibitor(s);

(8) a pharmaceutical composition as (7), wherein the water-soluble HMG-CoA reductase inhibitor is selected from the group consisting of pravastatin or a derivative thereof and rosuvastatin or a derivative thereof;

(9) a pharmaceutical composition as (7), wherein the water-soluble HMG-CoA reductase inhibitor is selected from the group consisting of pravastatin and rosuvastatin;

(10) a pharmaceutical composition as (7), wherein the water-soluble HMG-CoA reductase inhibitor is pravastatin;

(11) a pharmaceutical composition for improving insulin resistance comprising as an active ingredient one or more water-soluble HMG-CoA reductase inhibitor(s);

(12) a pharmaceutical composition as (11), wherein the water-soluble HMG-CoA reductase inhibitor is selected from the group consisting of pravastatin or a derivative thereof and rosuvastatin or a derivative thereof;

(13) a pharmaceutical composition as (11), wherein the water-soluble HMG-CoA reductase inhibitor is selected from the group consisting of pravastatin and rosuvastatin;

(14) a pharmaceutical composition as (11), wherein the water-soluble HMG-CoA reductase inhibitor is pravastatin;

(15) a pharmaceutical composition for the treatment or prevention of Syndrome X or metabolic syndrome comprising as an active ingredient one or more HMG-CoA reductase inhibitor(s);
(16) a pharmaceutical composition as (15), wherein the HMG-CoA reductase inhibitor is selected from the group consisting of pravastatin, lovastatin, simvastatin, fluvastatin, cerivastatin, atorvastatin, pitavastatin and rosuvastatin;
(17) a pharmaceutical composition as (15), wherein the HMG-CoA reductase inhibitor is a water-soluble HMG-CoA reductase inhibitor;
(18) a pharmaceutical composition as (15), wherein the HMG-CoA reductase inhibitor is selected from the group consisting of pravastatin or a derivative thereof and rosuvastatin or a derivative thereof;
(19) a pharmaceutical composition as (15), wherein the HMG-CoA reductase inhibitor is selected from the group consisting of pravastatin and rosuvastatin;
(20) a pharmaceutical composition as (15), wherein the HMG-CoA reductase inhibitor is pravastatin;
(21) a pharmaceutical composition for the treatment or prevention of hypertension comprising as an active ingredient one or more water-soluble HMG-CoA reductase inhibitor(s);
(22) a pharmaceutical composition as (21), wherein the water-soluble HMG-CoA reductase inhibitor is selected from the group consisting of pravastatin or a derivative thereof and rosuvastatin or a derivative thereof;
(23) a pharmaceutical composition as (21), wherein the water-soluble HMG-CoA reductase inhibitor is selected from the group consisting of pravastatin and rosuvastatin;
(24) a pharmaceutical composition as (21), wherein the water-soluble HMG-CoA reductase inhibitor is pravastatin;
(25) a pharmaceutical composition for the treatment or prevention of obesity comprising as an active ingredient one or more water-soluble HMG-CoA reductase inhibitor(s);
(26) a pharmaceutical composition as (25), wherein the water-soluble HMG-CoA reductase inhibitor is selected from the group consisting of pravastatin or a derivative thereof and rosuvastatin or a derivative thereof;
(27) a pharmaceutical composition as (25), wherein the water-soluble HMG-CoA reductase inhibitor is selected from the group consisting of pravastatin and rosuvastatin;
(28) a pharmaceutical composition as (25), wherein the water-soluble HMG-CoA reductase inhibitor is pravastatin;
(29) a pharmaceutical composition for the treatment of arteriosclerosis comprising as an active ingredient one or more water-soluble HMG-CoA reductase inhibitor(s);
(30) a pharmaceutical composition as (29), wherein the water-soluble HMG-CoA reductase inhibitor is selected from the group consisting of pravastatin or a derivative thereof and rosuvastatin or a derivative thereof;
(31) a pharmaceutical composition as (29), wherein the water-soluble HMG-CoA reductase inhibitor is selected from the group consisting of pravastatin and rosuvastatin;
(32) a pharmaceutical composition as (29), wherein the water-soluble HMG-CoA reductase inhibitor is pravastatin;
(33) a pharmaceutical composition for the treatment or prevention of diabetes, diabetes complications (including retinopathy, nephropathy, neuropathy, cataract and coronary artery disease), hypertension, obesity or arteriosclerosis caused by hypoadiponectinemia, comprising as an active ingredient one or more water-soluble HMG-CoA reductase inhibitor(s);
(34) a pharmaceutical composition as (33), wherein the water-soluble HMG-CoA reductase inhibitor is selected from the group consisting of pravastatin or a derivative thereof and rosuvastatin or a derivative thereof;
(35) a pharmaceutical composition as (33), wherein the water-soluble HMG-CoA reductase inhibitor is selected from the group consisting of pravastatin and rosuvastatin;
(36) a pharmaceutical composition as (33), wherein the water-soluble HMG-CoA reductase inhibitor is pravastatin;
(37) a pharmaceutical composition for the treatment or prevention of hypertension, obesity or arteriosclerosis caused by insulin resistance syndrome, comprising as an active ingredient one or more water-soluble HMG-CoA reductase inhibitor(s);
(38) a pharmaceutical composition as (37), wherein the water-soluble HMG-CoA reductase inhibitor is selected from the group consisting of pravastatin or a derivative thereof and rosuvastatin or a derivative thereof;
(39) a pharmaceutical composition as (37), wherein the water-soluble HMG-CoA reductase inhibitor is selected from the group consisting of pravastatin and rosuvastatin;
(40) a pharmaceutical composition as (37), wherein the water-soluble HMG-CoA reductase inhibitor is pravastatin;
(41) a method for enhancement of adiponectin production comprising administration of an effective amount of one or more HMG-CoA reductase inhibitor(s) to a warm-blooded animal;
(42) a method for treatment or prevention of Syndrome X or metabolic syndrome comprising administration of an effective amount of one or more HMG-CoA reductase inhibitor(s) to a warm-blooded animal;
(43) a method as (41) or (42), wherein the HMG-CoA reductase inhibitor is selected from the group consisting of pravastatin, lovastatin, simvastatin, fluvastatin, cerivastatin, atorvastatin, pitavastatin and rosuvastatin;
(44) a method as (41) or (42), wherein the HMG-CoA reductase inhibitor is a water-soluble HMG-CoA reductase inhibitor;
(45) a method as (41) or (42), wherein the HMG-CoA reductase inhibitor is selected from the group consisting of pravastatin or a derivative thereof and rosuvastatin or a derivative thereof;
(46) a method as (41) or (42), wherein the HMG-CoA reductase inhibitor is selected from the group consisting of pravastatin and rosuvastatin;
(47) a method as (41) or (42), wherein the HMG-CoA reductase inhibitor is pravastatin;
(48) a method for treatment or prevention of hypoadiponectinemia comprising administration of an effective amount of one or more water-soluble HMG-CoA reductase inhibitor(s) to a warm-blooded animal;
(49) a method for improving insulin resistance comprising administration of an effective amount of one or more water-soluble HMG-CoA reductase inhibitor(s) to a warm-blooded animal;
(50) a method for treatment or prevention of hypertension comprising administration of one or more water-soluble HMG-CoA reductase inhibitor(s) to a warm-blooded animal;
(51) a method for treatment or prevention of obesity comprising administration of one or more water-soluble HMG-CoA reductase inhibitor(s) to a warm-blooded animal;
(52) a method for treatment of arteriosclerosis comprising administration of one or more water-soluble HMG-CoA reductase inhibitor(s) to a warm-blooded animal;
(53) a method for treatment or prevention of diabetes, diabetes complications (including retinopathy, nephropathy, neuropathy, cataract and coronary artery disease), hypertension, obesity or arteriosclerosis caused by hypoadiponectinemia comprising administration of one or more water-soluble HMG-CoA reductase inhibitor(s) to a warm-blooded animal;

(54) a method for treatment or prevention of hypertension, obesity or arteriosclerosis caused by insulin resistance syndrome comprising administration of one or more water-soluble HMG-CoA reductase inhibitor(s) to a warm-blooded animal;
(55) a method as any one of (48) to (54), wherein the water-soluble HMG-CoA reductase inhibitor is selected from the group consisting of pravastatin and rosuvastatin;
(56) a method as any one of (48) to (54), wherein the water-soluble HMG-CoA reductase inhibitor is pravastatin; and,
(57) a method as any one of (41) to (56), wherein the warm-blooded animal is a human.

There are no particular restrictions on the HMG-CoA reductase inhibitor(s) serving as an active ingredient compound of the present invention provided it is a compound that demonstrates HMG-CoA reductase inhibitory action, examples of which include compounds having HMG-CoA reductase inhibitory action, pharmacologically acceptable salts thereof, or pharmacologically acceptable esters thereof as described in Japanese Patent Application (Kokai) No. Sho 57-2240 (U.S. Pat. No. 4,346,227), Japanese Patent Application (Kokai) No. Sho 57-163374 (U.S. Pat. No. 4,231,938), Japanese Patent Application (Kokai) No. Sho 56-122375 (U.S. Pat. No. 4,444,784), Japanese Patent Application (Kokai) No. Sho 60-500015 (U.S. Pat. No. 4,739,073), Japanese Patent Application (Kokai) No. Hei 1-216974 (U.S. Pat. No. 5,006,530), Japanese Patent Application (Kokai) No. Hei 3-58967 (U.S. Pat. No. 5,273,995), Japanese Patent Application (Kokai) No. Hei 1-279866 (U.S. Pat. Nos. 5,854,259 and 5,856,336) or Japanese Patent Application (Kokai) No. Hei 5-178841 (U.S. Pat. No. 5,260,440), preferably pravastatin, lovastatin, simvastatin, fluvastatin, cerivastatin, atorvastatin, pitavastatin or rosuvastatin, more preferably pravastatin or rosuvastatin, and most preferably pravastatin.

For an HMG-CoA reductase inhibitor serving as an active ingredient compound of the present invention, a water-soluble HMG-CoA reductase inhibitor such as pravastatin and rosuvastatin is preferable. In the present invention, a water-soluble HMG-CoA reductase inhibitor is an HMG-CoA reductase inhibitor in which the logarithm of the partition coefficient measured between phosphate buffer solution (pH 7.0 to 8.0, preferably pH 7.0 to 7.5, and more preferably pH 7.0) and 1-octanol [log(test substance concentration in 1-octanol phase/test substance concentration in buffer solution phase)] is 1.0 or less (preferably 0.5 or less, and more preferably 0.0 or less) (McTaggart, F. et al., The American Journal of Cardiology, 2001, 87, 28B-32B; Chapman, M. J. et al., Atherosclerosis Supplements, 2002, 33-37; Shimada, Y. et al., Progress in Medicine, 1998, 18, 957-962). The aforementioned partition coefficient can be measured according to ordinary methods (Partition Coefficient (n-octanol/water), OECD Guidelines for Testing of Chemicals, Section 1, Physical Chemical Properties, Paris, 1981, 107; Shimada, Y. et al., Progress in Medicine, 1998, 18, 957-962) or similar methods thereto.

In addition, for an HMG-CoA reductase inhibitor serving as an active ingredient compound of the present invention, pravastatin or derivative thereof, or rosuvastatin or derivative thereof, is preferable. In the present invention, a derivative of pravastatin is a compound having HMG-CoA reductase inhibitory action, a pharmacologically acceptable salt thereof or ester thereof as described in Japanese Patent Application (Kokai) No. Sho 57-2240 (U.S. Pat. No. 4,346,227), while a derivative of rosuvastatin is a compound having HMG-CoA reductase inhibitory action, a pharmacologically acceptable salt thereof or ester thereof as described in Japanese Patent Application (Kokai) No. Hei 5-178841 (U.S. Pat. No. 5,260,440).

Pravastatin is (+)-(3R,5R)-3,5-dihydroxy-7-[(1S,2S,6S,8S,8aR)-6-hydroxy-2-methyl-8-[(S)-2-methylbutyryloxy]-1,2,6,7,8,8a-hexahydro-1-naphthyl]heptanoic acid, and includes its pharmacologically acceptable salts or esters (for example, monosodium salt of the aforementioned pravastatin, etc.) as described in Japanese Patent Application (Kokai) No. Sho 57-2240 (U.S. Pat. No. 4,346,227). Lovastatin is (+)-(1S,3R,7S,8S,8aR)-1,2,3,7,8,8a-hexahydro-3,7-dimethyl-8-[2-[(2R,4R)-tetrahydro-4-hydroxy-6-oxo-2H-pyran-2-yl]ethyl]-1-naphthyl (S)-2-methylbutyrate, and includes its pharmacologically acceptable salts or esters as described in Japanese Patent Application (Kokai) No. Sho 57-163374 (U.S. Pat. No. 4,231,938). Simvastatin is (+)-(1S,3R,7S,8S,8aR)-1,2,3,7,8,8a-hexahydro-3,7-dimethyl-8-[2-[(2R,4R)-tetrahydro-4-hydroxy-6-oxo-2H-pyran-2-yl]ethyl]-1-naphthyl 2,2-dimethylbutyrate, and includes its pharmacologically acceptable salts or esters as described in Japanese Patent Application (Kokai) No. Sho 56-122375 (U.S. Pat. No. 4,444,784). Fluvastatin is (±)-(3R*,5S*,6E)-7-[3-(4-fluorophenyl)-1-(1-methylethyl)-1H-indol-2-yl]-3,5-dihydroxy-6-heptenoic acid, and includes its pharmacologically acceptable salts or esters (for example, monosodium salt of the aforementioned fluvastatin, etc.) as described in Japanese Patent Application (Kokai) No. Sho 60-500015 (U.S. Pat. No. 4,739,073). Cerivastatin is (3R,5S,6E)-7-[4-(4-fluorophenyl)-2,6-di-(1-methylethyl)-5-methoxymethylpyridin-3-yl]-3,5-dihydroxy-6-heptenoic acid, and includes its pharmacologically acceptable salts or esters (for example, monosodium salt of the aforementioned cerivastatin, etc.) as described in Japanese Patent Application (Kokai) No. Hei 1-216974 (U.S. Pat. No. 5,006,530). Atorvastatin is (3R,5S)-7-[2-(4-fluorophenyl)-5-(1-methylethyl)-3-phenyl-4-phenylaminocarbonyl-1H-pyrrol-1-yl]-3,5-dihydroxyheptanoic acid, and includes its pharmacologically acceptable salts or esters (for example, ½ calcium salt of the aforementioned atorvastatin, etc.) as described in Japanese Patent Application (Kokai) No. Hei 3-58967 (U.S. Pat. No. 5,273,995). Pitavastatin is (E)-3,5-dihydroxy-7-[4'-(4"-fluorophenyl)-2'-cyclopropylquinolin-3'-yl]-6-heptenoic acid, and includes its pharmacologically acceptable salts or esters (for example, ½ calcium salt of the aforementioned pitavastatin, etc.) as described in Japanese Patent Application (Kokai) No. Hei 1-279866 (U.S. Pat. Nos. 5,854,259 and 5,856,336). Rosuvastatin is (+)-(3R,5S)-7-[4-(4-fluorophenyl)-6-isopropyl-2-(N-methyl-N-methanesulfonylamino)pyrimidin-5-yl]-3,5-dihydroxy-6(E)-heptenoic acid, and includes its pharmacologically acceptable salts or esters (for example, ½ calcium salt of the aforementioned rosuvastatin, etc.) as described in Japanese Patent Application (Kokai) No. Hei 5-178841 (U.S. Pat. No. 5,260,440).

The following indicates the two-dimensional structural formulas of major HMG-CoA reductase inhibitors.

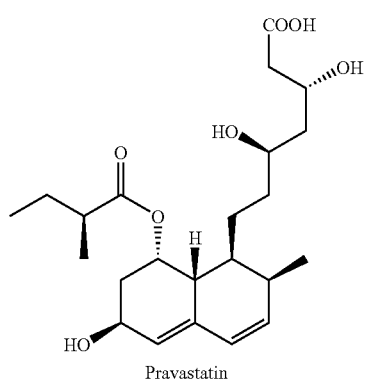
Pravastatin

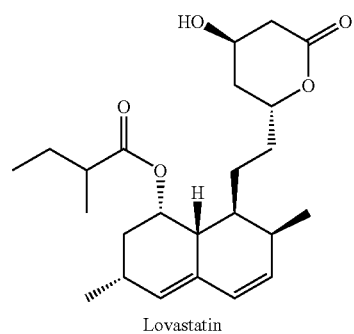
Lovastatin

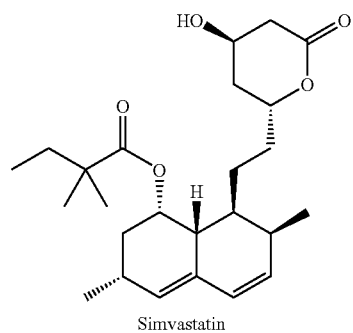
Simvastatin

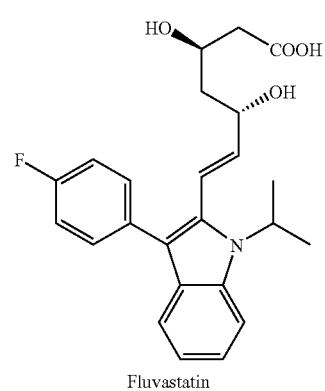
Fluvastatin

-continued

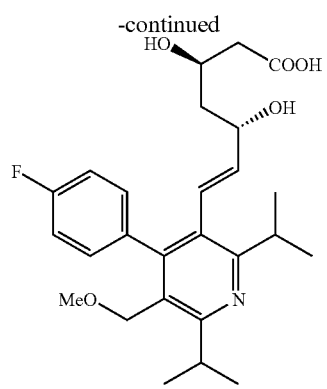
Cerivastatin

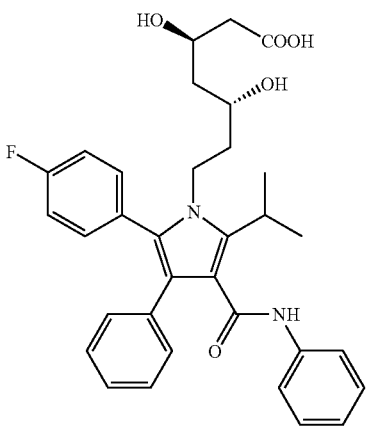
Atorvastatin

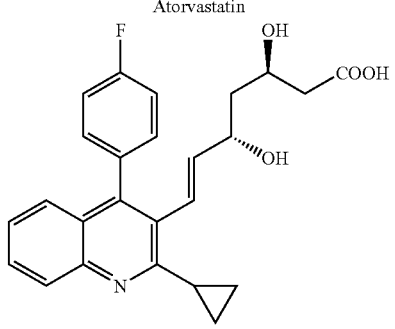
Pitavastatin

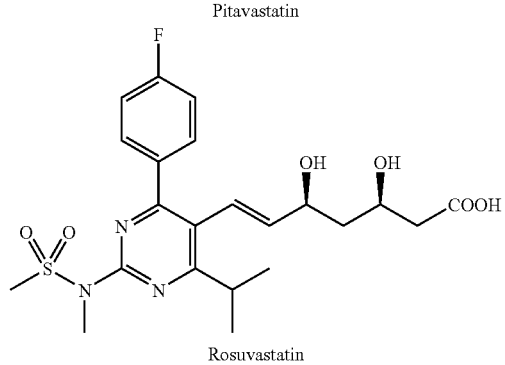
Rosuvastatin

In the case where the aforementioned HMG-CoA reductase inhibitor has an asymmetric carbon, all of its racemate, its optical isomers and mixtures thereof are included in the HMG-CoA reductase inhibitor of the present invention. In addition, hydrates of the aforementioned HMG-CoA reductase inhibitors are also included in the HMG-CoA reductase inhibitor of the present invention.

For an HMG-CoA reductase inhibitor serving as an active ingredient compound in the present invention, one type of compound can be used alone, or a mixture of two or more types of compounds can be used. In the case of using a mixture of two or more types of compounds, the compounds can be used simultaneously or each of compounds can be used separately at different times.

An HMG-CoA reductase inhibitor serving as an active ingredient of the present invention can easily be prepared in accordance with known methods [for example, Japanese Patent Application (Kokai) No. Sho 57-2240 (U.S. Pat. No. 4,346,227), Japanese Patent Application (Kokai) No. Sho 57-163374 (U.S. Pat. No. 4,231,938), Japanese Patent Application (Kokai) No. Sho 56-122375 (U.S. Pat. No. 4,444,784), Japanese Patent Application (Kokai) No. Sho 60-500015 (U.S. Pat. No. 4,739,073), Japanese Patent Application (Kokai) No. Hei 1-216974 (U.S. Pat. No. 5,006,530), Japanese Patent Application (Kokai) No. Hei 3-58967 (U.S. Pat. No. 5,273,995), Japanese Patent Application (Kokai) No. Hei 1-279866 (U.S. Pat. Nos. 5,854,259 and 5,856,336), Japanese Patent Application (Kokai) No. Hei 5-178841 (U.S. Pat. No. 5,260,440), etc.] or similar methods thereto.

INDUSTRIAL APPLICABILITY

In the case of using the HMG-CoA reductase inhibitor(s) serving as an active ingredient of the present invention as a pharmaceutical (pharmaceutical composition for treatment or prevention of the aforementioned diseases), it can be administered in the form of a bulk medicament of the pharmaceutical itself; or it can be orally administered in a formulation such as tablet, capsule, granules, pill, powder, liquid, syrup, troche, suspension, emulsion, etc. or be parenterally administered in a formulation such as an injection, suppository or patch, etc., which formulations are made by mixing the HMG-CoA reductase inhibitor with a suitably pharmacologically acceptable excipient, binder and so forth. An oral administration is preferred.

These formulations are prepared using well-known methods using additives such as excipients, binders, disintegrants, lubricants, emulsifiers, stabilizers, corrigents, diluents, injection solvents and so forth.

An excipient may be, for example, an organic excipient or inorganic excipient. Examples of organic excipients include sugar derivatives such as lactose, sucrose, glucose, mannitol and sorbitol; starch derivatives such as cornstarch, potato starch, alpha starch, dextrin and carboxymethyl starch; cellulose derivatives such as crystalline cellulose, hydroxypropyl cellulose, low substituted hydroxypropyl cellulose, hydroxypropylmethyl cellulose, carboxymethyl cellulose, calcium carboxymethyl cellulose, and internally-crosslinked sodium carboxymethyl cellulose; gum arabic; dextran; and, pullulan. Examples of inorganic excipients include silicic acid salt derivatives such as light anhydrous silicic acid, synthetic aluminum silicate, calcium silicate, and magnesium metasilicate aluminate; phosphoric acid salts such as calcium phosphate; carbonic acid salts such as calcium carbonate; and sulfuric acid salts such as calcium sulfate.

Examples of binders include the compounds as described for the aforementioned excipient; gelatin; polyvinylpyrrolidone; and, polyethylene glycol.

Examples of disintegrants include the compounds as described for the aforementioned excipient; chemically modified starch or cellulose derivatives such as crosscarmelose sodium and sodium carboxymethyl starch; and, crosslinked polyvinylpyrrolidone.

Examples of lubricants include talc; stearic acid; metal stearates such as calcium stearate and magnesium stearate; colloidal silica; waxes such as bee gum and spermaceti; boric acid; glycol; DL-leucine; carboxylic acids such as fumaric acid and adipic acid; carboxylic acid sodium salts such as sodium benzoate; sulfates such as sodium sulfate; lauryl sulfates such as sodium lauryl sulfate and magnesium lauryl sulfate; silicic acids such as anhydrous silicic acid and silicic acid hydrate; and the above starch derivatives as for the aforementioned excipients.

Examples of emulsifiers include colloidal clays such as bentonite and bee gum; metal hydroxides such as magnesium hydroxide and aluminium hydroxide; anionic surfactants such as sodium lauryl sulfate and calcium stearate; cationic surfactants such as benzalkonium chloride; and, nonionic surfactants such as polyoxyethylene alkyl ether, polyoxyethylene sorbitan fatty acid ester, and sucrose fatty acid ester.

Examples of stabilizers include parahydroxybenzoic acid esters such as methyl paraben and propyl paraben; alcohols such as chlorobutanol, benzyl alcohol and phenylethyl alcohol; benzalkonium chloride; phenols such as phenol and cresol; thimerosal; dehydroacetic acid; and sorbic acid.

Examples of corrigents include ordinarily used sweeteners, sour flavourings, fragrances, etc.

Examples of diluents include water, ethanol, propylene glycol, ethoxyisostearyl alcohol and polyoxyethylene sorbitan fatty acid ester.

Examples of injection solvents include water, ethanol and glycerin.

The HMG-CoA reductase inhibitor(s) serving as an active ingredient of the present invention can be administered to a warm-blooded animal (and particularly a human). The dose can be varied depending on various conditions such as the symptoms and age of the patient. In the case of oral administration, 0.1 mg (preferably 0.5 mg) as a lower limit and 1000 mg (preferably 500 mg) as an upper limit can be administered once to six times per day for a human adult depending on the symptoms. In the case of parenteral administration, 0.01 mg (preferably 0.05 mg) as a lower limit and 100 mg (preferably 50 mg) as an upper limit can be administered once to six times per day for a human adult depending on the symptoms.

Since the HMG-CoA reductase inhibitor(s) serving as an active ingredient of the present invention has superior adiponectin production enhancing action, it is useful as a pharmaceutical composition for the treatment or prevention of diseases wherein blood adiponectin concentration decreases due to the occurrence of that disease, and diseases that occur due to a decrease in blood adiponectin concentration (and preferably diseases wherein blood adiponectin concentration decreases due to the occurrence of that disease).

The HMG-CoA reductase inhibitor(s) serving as an active ingredient of the present invention is useful as a pharmaceutical composition for enhancement of adiponectin production; treatment or prevention of hypoadiponectinemia; improvement of insulin resistance; treatment or prevention of Syndrome X or metabolic syndrome; treatment or prevention of diabetes, diabetes complications (including retinopathy, nephropathy, neuropathy, cataract and coronary artery disease), hypertension, obesity or arteriosclerosis; or, treatment or prevention of diabetes, diabetes complications (including retinopathy, nephropathy, neuropathy, cataract and coronary artery disease), hypertension, obesity or arteriosclerosis caused by hypoadiponectinemia or insulin resistance syndrome, preferably for enhancement of adiponectin production; treatment or prevention of hypoadiponectinemia; improvement of insulin resistance; or treatment or prevention of diabetes, diabetes complications (including retinopathy, nephropathy, neuropathy, cataract and coronary artery disease), hypertension, obesity or arteriosclerosis caused by hypoadiponectinemia or insulin resistance syndrome, more preferably for enhancement of adiponectin production; treatment or prevention of hypoadiponectinemia; or treatment or prevention of diabetes or arteriosclerosis caused by hypoadiponectinemia, and even more preferably for enhancement of adiponectin production or treatment or prevention of hypoadiponectinemia.

In addition, the aforementioned pharmaceutical composition is preferably for warm-blooded animals, and more preferably for humans. A pharmaceutical composition for treatment or prevention of the present invention is preferably a pharmaceutical composition for treatment.

BEST MODE FOR CARRYING OUT THE INVENTION

The following provides a more detailed explanation of the present invention by indicating Examples and Formulation examples, but the present invention is not limited thereto.

Example 1

Adiponectin Production Enhancing Action (In Vitro)

(1) Cell Culturing

Preadipocyte cell line 3T3-L1 was purchased from the American Type Culture Collection (ATCC). The 3T3-L1 cells were plated onto a 24-well, collagen-coated plate and cultured to saturation in growth medium (DMEM, 25 mM glucose, 10% FCS, 100 u/ml penicillin, 0.1 mg/ml streptomycin) under conditions of 37° C. and 5% $CO_2$. Five days after cell proliferation had reached a saturated state, the medium was replaced with medium (DMEM, 25 mM glucose, 10% FCS, 100 u/ml penicillin, 0.1 mg/ml streptomycin) to which had been added 1 µM insulin, 0.5 mM 3-isobutyl-1-methylxanthine and 1 µM dexamethazone to initiate adipocyte differentiation. Two days later, the medium was replaced with growth medium containing 1 µM insulin followed by additionally culturing the cells for 2 days. Subsequently, the medium was replaced with fresh growth medium every 3 days, and the 3T3-L1 adipocytes were prepared on day 10 after the start of differentiation.

Test compounds that were poorly soluble in water were used after dissolving in DMSO. Test compounds that were easily soluble in water were dissolved in sterile water followed by addition of the same amount of DMSO as that used for the aforementioned poorly water-soluble test compounds. In addition, in the case of test compounds that are poorly soluble in water, the test compound may be dissolved in ethanol and used following the addition of 0.1 N aqueous sodium hydroxide solution after shaking as necessary.

After allowing the 3T3-L1 cells to adequately differentiate into adipocytes, a test compound was added to the medium to a final concentration of 10 µM followed by culturing the cells for 48 hours. The cells were additionally cultured for 24 hours after replacing the medium. Following culturing, the cells were used for measurement of adiponectin mRNA, while the supernatant used for measurement of the amount of adiponectin secreted.

(2) Measurement of Adiponectin mRNA

RNA was extracted from cells that had been treated with a test compound using Sepasol (Nacalai-Tesque). cDNA was then synthesized using the ThermoScript Reverse Transcriptase Kit (registered trade mark: Invitrogen) by using the extracted RNA as a template. The synthesized cDNA was amplified using FastStrand DNA Master SYBR Green I (Roche Diagnostics), and the amplified PCR product was detected with LightCycler (Roche Diagnostics). The sequences and SEQ ID numbers in the sequence listing to be described later for the primers used and the 36B4 used as an internal control are shown below.

```
Adiponectin:
5'-GATGGCAGAGATGGCACTCC-3'
(SEQ ID NO. 1: adiponectin PCR primer)

5'-CTTGCCAGTGCTGCGGTCAT-3'
(SEQ ID NO. 2: adiponectin PCR primer)

36B4:
5'-GCTCCAAGCAGATGCAGCA-3'
(SEQ ID NO. 3: 36B4 PCR primer)

5'-CCGGATGTGAGGCAGCAG-3'
(SEQ ID NO. 4: 36B4 PCR primer)
```

The adiponectin mRNA amount was measured according to quantitative RT-PCR. The amounts of adiponectin mRNA in the groups in which pravastatin and rosuvastatin were used as test compounds were 1.6 times and 1.3 times higher, respectively, than those in the control group.

(3) Measurement of Amount of Secreted Adiponectin

Secretion of adiponectin into culture supernatant was detected by Western blotting. 0.5 µl of recovered culture supernatant were fractionated by 12.5% SDS-polyacrylamide gel electrophoresis, and the protein following fractionation was transferred to a PVDF membrane (Millipore). Subsequently, anti-adiponectin antibody was bound to the PVDF membrane and after washing with PBS, was reacted with antibody conjugated with Horseradish peroxidase. After washing the PVDF membrane, the adiponectin bands were detected using ECL Detection Reagents (Amersham-Pharmacia). The bands were quantified with a densitometer (Molecular Devices).

The amounts of secreted adiponectin were analyzed by Western blotting. The amounts of secreted adiponectin in the groups in which pravastatin and rosuvastatin were used as test compounds were 1.7 times and 1.6 times higher, respectively, than those in the control group.

On the basis of the results described in (2) and (3) above, an HMG-CoA reductase inhibitor serving as an active ingredient of the present invention was determined to have superior action of enhancing the production of adiponectin, and to be useful as a pharmaceutical composition for enhancement of adiponectin production; treatment or prevention of hypoadiponectinemia; improvement of insulin resistance; treatment or prevention of diabetes, diabetes complications (including retinopathy, nephropathy, neuropathy, cataract and coronary artery disease), hypertension, obesity or arteriosclerosis caused by hypoadiponectinemia or insulin resistance syndrome; etc.

Example 2

Adiponectin Production Enhancing Action (In Vivo) and Glucose Uptake Enhancing Action (1) Administration of Pravastatin to Mice in Feed
(i) Test Animals C57BL/6J mice (male, age 5 weeks) were purchased from Clea Japan, and used in the test after acclimating to the test environment for 1 week. The mice were housed 5 animals to a cage and given unrestricted access to feed (F2, Funabashi farm) and water.

(ii) Schedule

The body weights of the animals were measured and blood samples were collected on the day the test started, and the animals were divided into two groups of 5 animals per cage based on their body weights and blood glucose levels. Blood samples were collected at the start of the test and in weeks 6, 11 and 15 after the start of the test. Blood samples were collected from the tail vein in an amount equal to one heparinized capillary tube.

(iii) Administration Method

Pravastatin powder was added to the F2 powder to 0.06% (wt/wt), uniformly mixed and provided to the animals in individual cages. The amount of feed and general behaviour were checked at least once a day.

(iv) Measurement

Blood glucose levels were measured on the days when blood samples were collected. Adiponectin levels were measured simultaneously for all blood samples following completion of administration. The Glucose CII-Test Wako (Wako) and Mouse/Rat Adiponectin ELISA Kit (Otsuka Pharmaceutical) were respectively used for measurement.

(2) Insulin Tolerance Test Using Pravastatin-Dosed Mice

A group administered with pravastatin by mixing in feed for 15 weeks and a non-dosed group of C57BL/6J mice (n=5) were fasted for 2 hours. After measuring the body weight of each animal, insulin (Humalin, Lilly) was administered intraperitoneally at 0.5 u/kg, and blood samples were collected from the tail vein immediately before the start of administration and at 15, 30, 60 and 90 minutes after the start of administration followed by measurement of blood glucose levels.

(3) Glucose Uptake Test Using Isolated Adipocytes from Pravastatin-Dosed Mice (i) Epididymal adipose tissue was excised from a group administered with pravastatin for 16 weeks and a non-dosed group of C57BL/6J mice (n=5). The excised adipose tissue was handled under conditions of 37° C. at all times. The adipose tissue was cut into small pieces with a scissors, followed by the addition of medium (DMEM, 1 mM sodium pyruvate, 25 mM HEPES pH 7.4, 0.1% BSA, 100 u/ml penicillin, 0.1 mg/ml streptomycin) containing 1 mg/ml of collagenase I (Worshington), and shaking at 37° C. and 80 rpm. Following the reaction, 2.5 volumes of the aforementioned medium were added, the adipocytes were screened out by passing the cell suspension through a 260 μm mesh sieve, and again passed through a 100 μm mesh sieve to prepare an adipocyte suspension.

(ii) The glucose uptake test was carried out in the manner as described below. 100 μl of the aforementioned cell suspension, 90 μl of medium and 10 μl of insulin solution were added to a polystyrene tube, while stirring gently to uniformly distribute the adipocytes in each tube, and the adipocytes cultured for 30 minutes at 30° C. Subsequently, 0.6 μCi of $^3$H-labeled 2-deoxyglucose was added and allowed to react for 30 minutes. Following the reaction, the cell suspension was immediately transferred to a centrifuge tube containing silicone oil and centrifuged. After cutting out the oil layer of the upper layer containing adipocytes with a knife, it was transferred to a glass vial containing 4 ml of Hionic Fluor (Perkin-Elmer) liquid scintillation counter cocktail followed by measurement of specific radioactivity. The amount of measured radioactivity of the $^3$H-2-deoxyglucose was used as an indicator of the amount of glucose taken up by the cells.

(4) Results

In (1) above, pravastatin was administered to C57BL/6J mice for 15 weeks followed by measurement of blood glucose levels and adiponectin concentrations. Adiponectin concentrations were measured in the same manner as Example 1. Although there were no significant differences in blood glucose levels between the pravastatin dose group and non-dose group, adiponectin concentrations in the dose group were 1.28 times higher than in the non-dose group.

In the insulin tolerance test described in (2) above, the pravastatin dose group demonstrated significantly lower blood glucose levels than the non-dose group at 60 minutes after administration of insulin (non-dose group blood glucose level: 148 mg/dl, dose group blood glucose level: 110 mg/dl).

In the C57BL/6J mouse adipocytes in (3) above, the pravastatin dose group demonstrated increased insulin sensitivity and increased glucose uptake more than the non-dose group. The amount of glucose uptake by the pravastatin dose group was 1.4 times greater than that by the non-dose group.

From the aforementioned results, an HMG-CoA reductase inhibitor serving as an active ingredient of the present invention was found to enhance adiponectin production, to increase insulin sensitivity and to enhance insulin-induced glucose uptake, and was determined to be useful as a pharmaceutical composition for the enhancement of adiponectin production; treatment or prevention of hypoadiponectinemia; improvement of insulin resistance; treatment or prevention of Syndrome X or metabolic syndrome; treatment or prevention of diabetes, diabetes complications (including retinopathy, nephropathy, neuropathy, cataract and coronary artery disease), hypertension, obesity or arteriosclerosis; or the treatment or prevention of diabetes, diabetes complications (including retinopathy, nephropathy, neuropathy, cataract and coronary artery disease), hypertension, obesity or arteriosclerosis caused by hypoadiponectinemia or insulin resistance syndrome.

Formulation Example 1

Tablets

After mixing 10 parts of pravastatin sodium, 71.55 parts of lactose, 20 parts of low substituted hydroxypropyl cellulose (LH21, Shin-Etsu Chemical), 20 parts of crystalline cellulose (Avicel PH101, Asahi Kasei) and 6.5 parts of magnesium metasilicate aluminate (Neusilin FL2, Fuji Chemical Industry) with a Henschel mixer (Mitsui Mining), 13 parts of a 10% aqueous solution of hydroxypropyl cellulose (Nippon Soda) and a suitable amount of water were added to the resulting mixture followed by kneading with a Henschel mixer. The resulting kneaded product was dried for 1 hour at 60° C. with an air dryer. The resulting dried product was sized with a power mill (Dalton) equipped with a 1 mm φ diameter screen, and 129.35 parts of the resulting granules and 0.65 parts of magnesium stearate (NOF Corporation) were mixed with a V-mixer (Tokuju Seisakusho). The resulting mixture was formed into tablets to produce tablets having a diameter of 7.0 mm.

The invention claimed is:

1. A method for increasing adiponectin production in a warm-blooded animal, consisting of administering to a warm-blooded animal in need of such treatment an effective amount of one or two water-soluble HMG-CoA reductase inhibitor(s), wherein the water-soluble HMG-CoA reductase inhibitor(s) are selected from the group consisting of pravastatin, rosuvastatin, and a combination of pravastatin and rosuvastatin.

2. The method according to claim 1, wherein the water-soluble HMG-CoA reductase inhibitor is pravastatin.

3. A method for treatment of hypoadiponectinemia in a warm-blooded animal, consisting of administering to a warm-blooded animal in need of such treatment an effective amount of one or two water-soluble HMG-CoA reductase inhibitor(s), wherein the water-soluble HMG-CoA reductase inhibitor(s) are selected from the group consisting of pravastatin, rosuvastatin, and a combination of pravastatin and rosuvastatin.

4. The method according to claim 3, wherein the water-soluble HMG-CoA reductase inhibitor is pravastatin.

5. The method according to claim 1, wherein the warm blooded animal is a human.

6. The method according to claim 2, wherein the warm-blooded animal is a human.

7. The method according to claim 3, wherein the warm-blooded animal is a human.

8. The method according to claim 4, wherein the warm-blooded animal is a human.

9. A method for increasing adiponectin production in a warm-blooded animal, consisting of administering to a warm-blooded animal in need of such treatment a composition consisting of an effective amount of one or two water-soluble HMG-CoA reductase inhibitor(s) and optionally one or more pharmacologically acceptable excipient(s), wherein the water-soluble HMG-CoA reductase inhibitor(s) are selected from the group consisting of pravastatin, rosuvastatin, and a combination of pravastatin and rosuvastatin.

10. The method according to claim 9, wherein the water-soluble HMG-CoA reductase inhibitor is pravastatin.

11. A method for treatment of hypoadiponectinemia in a warm-blooded animal, consisting of administering to a warm-blooded animal in need of such treatment a composition consisting of an effective amount of one or two water-soluble HMG-CoA reductase inhibitor(s) and optionally one or more pharmacologically acceptable excipient(s), wherein the water-soluble HMG-CoA reductase inhibitor(s) are selected from the group consisting of pravastatin, rosuvastatin, and a combination of pravastatin and rosuvastatin.

12. The method according to claim 11, wherein the water-soluble HMG-CoA reductase inhibitor is pravastatin.

* * * * *

SEQUENCE LISTING

```
<160> NUMBER OF SEQ ID NOS: 4

<210> SEQ ID NO 1
<211> LENGTH: 20
<212> TYPE: DNA
<213> ORGANISM: Artificial Sequence
<220> FEATURE:
<223> OTHER INFORMATION: An adiponectin PCR primer.

<400> SEQUENCE: 1
gatggcagag atggcactcc                                                      20

<210> SEQ ID NO 2
<211> LENGTH: 20
<212> TYPE: DNA
<213> ORGANISM: Artificial Sequence
<220> FEATURE:
<223> OTHER INFORMATION: An adiponectin PCR primer.

<400> SEQUENCE: 2
cttgccagtg ctgcggtcat                                                      20

<210> SEQ ID NO 3
<211> LENGTH: 19
<212> TYPE: DNA
<213> ORGANISM: Artificial Sequence
<220> FEATURE:
<223> OTHER INFORMATION: A 36B4 PCR primer.

<400> SEQUENCE: 3
gctccaagca gatgcagca                                                       19

<210> SEQ ID NO 4
<211> LENGTH: 18
<212> TYPE: DNA
<213> ORGANISM: Artificial Sequence
<220> FEATURE:
<223> OTHER INFORMATION: A 36B4 PCR primer.

<400> SEQUENCE: 4
ccggatgtga ggcagcag                                                        18
```